US012767650B2

(12) United States Patent
Leng et al.

(10) Patent No.: US 12,767,650 B2
(45) Date of Patent: Oct. 20, 2026

(54) CRYSTAL FORM OF ENTRECTINIB AND PREPARATION METHOD THEREFOR

(71) Applicant: QILU PHARMACEUTICAL CO., LTD., Jinan (CN)

(72) Inventors: Chuanxin Leng, Jinan (CN); Huicheng Wang, Jinan (CN); Xi Fang, Jinan (CN); Chuanwen Fan, Jinan (CN); Dong Lin, Jinan (CN); Tao Liu, Jinan (CN); Zhaowei Huang, Jinan (CN); Fang Cheng, Jinan (CN); Shuailong Huang, Jinan (CN)

(73) Assignee: QILU PHARMACEUTICAL CO., LTD., Jinan (CN)

( * ) Notice: Subject to any disclaimer, the term of this patent is extended or adjusted under 35 U.S.C. 154(b) by 508 days.

(21) Appl. No.: 18/263,799

(22) PCT Filed: Jan. 24, 2022

(86) PCT No.: PCT/CN2022/073475

§ 371 (c)(1),
(2) Date: Aug. 1, 2023

(87) PCT Pub. No.: WO2022/166647

PCT Pub. Date: Aug. 11, 2022

(65) Prior Publication Data

US 2024/0308990 A1 Sep. 19, 2024

(30) Foreign Application Priority Data

Feb. 3, 2021 (CN) ........................ 202110150771.9

(51) Int. Cl.
*C07D 405/14* (2006.01)

(52) U.S. Cl.
CPC .................................. *C07D 405/14* (2013.01)

(58) Field of Classification Search
CPC .................................................... C07D 405/14
See application file for complete search history.

(56) References Cited

U.S. PATENT DOCUMENTS

2020/0216427 A1 7/2020 Matecic Musanic

FOREIGN PATENT DOCUMENTS

| | | | | | |
|---|---|---|---|---|---|
| CN | 104395308 A | | 3/2015 | | |
| CN | 109153669 A | | 1/2019 | | |
| CN | 111171009 A | * | 5/2020 | .............. | A61P 35/00 |
| CN | 113354626 A | | 9/2021 | | |
| WO | 2013174876 A1 | | 11/2013 | | |
| WO | 2017202674 A1 | | 11/2017 | | |
| WO | 2021084260 A1 | | 5/2021 | | |

* cited by examiner

*Primary Examiner* — Jeffrey H Murray
*Assistant Examiner* — Kristen W Romero
(74) *Attorney, Agent, or Firm* — NKL Law; Allen Xue

(57) ABSTRACT

Crystal forms of Entrectinib and preparation method therefor, such as crystal form A and crystal form B of Entrectinib are provided. Compared with existing crystal forms of Entrectinib, the crystal form has better solubility, chemical and crystal form stability, is free of static electricity, has good fluidity, is easy for large-scale preparation, and can be better suitable for preparing pharmaceutical formulations and large-scale production.

7 Claims, 7 Drawing Sheets

CRYSTAL FORM OF ENTRECTINIB AND PREPARATION METHOD THEREFOR

CROSS-REFERENCE TO RELATED APPLICATIONS

This application is a U.S. national stage entry of PCT International Application No. PCT/CN2022/073475, filed on Jan. 24, 2022, which claims priority to the prior application of patent application No. 202110150771.9 filed to the China National Intellectual Property Administration on Feb. 3, 2021 and entitled "CRYSTAL FORM OF ENTRECTINIB AND PREPARATION METHOD THEREFOR", the content of which is incorporated herein by reference in its entirety.

TECHNICAL FIELD

The present disclosure belongs to the technical field of pharmaceutical chemistry, and in particular relates to a novel crystal form of entrectinib, and a preparation method therefor, and use thereof.

BACKGROUND

Entrectinib, chemically known as N-[5-(3,5-difluorobenzyl)-1H-indazol-3-yl]-4-(4-methylpiperazin-1-yl)-2-[(tetrahydro-2H-pyran-4-yl)amino]benzamide, is used for the treatment of adult and pediatric patients with advanced recurrent solid tumors that are positive for neurotrophic tyrosine receptor kinase (NTRK) fusion. Rozlytrek is the first drug approved in Japan for targeting NTRK gene fusion tumors, in a range of solid tumor types which are difficult to treat, including pancreatic cancer, thyroid cancer, salivary gland cancer, breast cancer, colorectal cancer, lung cancer, and the like.

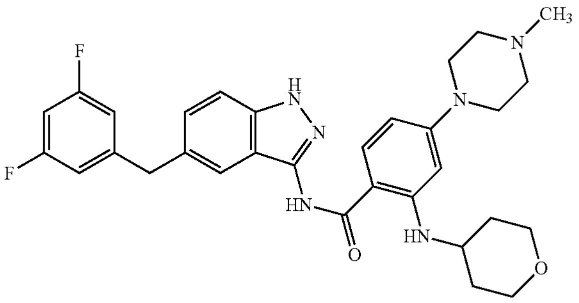

Entrectinib

Various crystal forms of entrectinib have been disclosed in the prior art documents. For example, the international patent application WO2013174876 of the original research company discloses crystal forms 1, 2 and 3 of entrectinib, wherein the crystal form 3 is a solvate of ethyl acetate and n-hexane; the International Patent Application WO2017202674 discloses a crystal form 4 of entrectinib; the Chinese Patent Application CN111171009A discloses 9 crystal forms from AZT-A to AZT-I, wherein the preferred crystal forms are the crystal form AZT-A, the crystal form AZT-B and the crystal form AZT-E.

The crystal forms 1, 2 and 4 are all crystallized using a mixed solvent of ethanol and water. Mixed crystals are easy to appear in the crystallization process, and the mixed crystals are ensured not to appear only by very precise control. Thus, the industrial production difficulty is greater. In addition, researches show that the crystal form 1 contains more amorphous forms, the crystallization system is viscous, the filtration is difficult, the large-scale production is not facilitated, the crystal form is unstable and is easy to be converted into another crystal form, and thus the crystal form is not suitable for medicinal use; the crystal form 3 is a solvate of ethyl acetate and n-hexane, the solvent content exceeds the limit required by ICH guidelines, and thus the crystal form is not suitable for medicinal use; the crystallization solvent of the crystal form 4 is the same as that of the crystal form 2, the crystal form 2 is easily obtained in the preparation process, and there are risks in the production; entrectinib is of BCS class 2, belongs to a low-solubility and high-permeability drug, has poor solubility of crystal form 2 and a large particle size, needs to be micronized, and has the problems of serious static electricity, poor fluidity and the like in the micronized samples, thereby affecting the production of formulations; the crystal forms AZT-A, AZT-B, and AZT-E have a large particle size and need to be micronized, and have the problems of serious static electricity, poor fluidity and the like in the micronized samples, that is, the uniformity of mixed powder of the API is affected, and has an adverse effect on the production of formulations.

Therefore, a novel crystal form of entrectinib, which has good stability and better solubility, exhibits no static electricity in the production process of API and formulations, has good fluidity, and is easy to realize large-scale production, is urgently needed to be found at present, and the production process needs to be stable and will not be converted into another crystal form or mixed crystal so as to make up for the defects in the prior art.

In order to overcome the defects of existing crystal forms of entrectinib in the art, the inventors carry out more intensive and extensive research on crystal forms of entrectinib. In the process, novel crystal forms of entrectinib are obtained, which have good stability, high purity and good solubility, no need for crushing, and no static electricity generation. The preparation method is suitable for large-scale production and is highly practicable, overcoming the defects in the prior art.

SUMMARY

An object of the present disclosure is to provide novel crystal forms of entrectinib, which have good stability, high purity, a simple preparation process, and high practicability, and a method for preparing the novel crystal forms.

A first aspect of the present disclosure provides a novel crystal form A of entrectinib, comprising characteristic diffraction peaks in an X-ray powder diffraction pattern using Cu-Kα radiation at 2θ angles of 7.1°±0.2°, 7.7°±0.2°, 8.5°±0.2°, 10.5°±0.2°, 13.9°±0.2°, 15.6°±0.2°, and 21.5°±0.2°.

Specifically, the crystal form A of entrectinib comprises characteristic diffraction peaks in an X-ray powder diffraction pattern using Cu-Kα radiation at 2θ angles of 7.1°±0.2°, 7.7°±0.2°, 8.5°±0.2°, 10.5°±0.2°, 13.2°±0.2°, 13.9°±0.2°, 14.4°±0.2°, 15.6°±0.2°, 21.5°±0.2°, 22.6°±0.2°, 23.5°±0.2°, 24.6°±0.2°, and 25.8°±0.2°;

more specifically, the crystal form A of entrectinib comprises characteristic diffraction peaks in an X-ray powder diffraction pattern using Cu-Kα radiation at 2θ angles of 7.1°±0.2°, 7.7°±0.2°, 8.5°±0.2°, 10.5°±0.2°, 13.2°±0.2°, 13.9°±0.2°, 14.4°±0.2°, 15.6°±0.2°, 17.2°±0.2°, 18.9°±0.2°, 19.6°±0.2°, 21.5°±0.2°, 22.6°±0.2°, 23.5°±0.2°, 24.6°±0.2°, and 25.8°±0.2°.

In a preferred embodiment of the present disclosure, the crystal form A of entrectinib has the following characteristic peaks and relative intensities under powder X-ray diffraction:

| 2θ | Relative intensity |
|---|---|
| 7.1° ± 0.2° | 53% |
| 7.7° ± 0.2° | 25% |
| 8.5° ± 0.2° | 78% |
| 10.5° ± 0.2° | 100% |
| 13.2° ± 0.2° | 13% |
| 13.9° ± 0.2° | 24% |
| 14.4° ± 0.2° | 15% |
| 15.6° ± 0.2° | 49% |
| 17.2° ± 0.2° | 44% |
| 18.9° ± 0.2° | 24% |
| 19.6° ± 0.2° | 28% |
| 21.5° ± 0.2° | 69% |
| 22.6° ± 0.2° | 30% |
| 23.5° ± 0.2° | 52% |
| 24.6° ± 0.2° | 42% |
| 25.8° ± 0.2° | 13% |

In a preferred embodiment of the present disclosure, the crystal form A of entrectinib has an X-ray powder diffraction pattern substantially as shown in FIG. 1.

Through determination, a DSC pattern of the crystal form A of entrectinib has endothermic peaks respectively at temperatures in the range of 122.0-159.8° C. and in the range of 193.2-206.4° C.;

specifically, peak values of the endothermic peaks respectively appear at 147.1±2° C. and 198.0±0.1° C.; more specifically, in one embodiment of the present disclosure, the crystal form A of entrectinib has a DSC pattern substantially as shown in FIG. 2.

In one technical solution of the present disclosure, the crystal form A of entrectinib has a TGA pattern substantially as shown in FIG. 2.

A second aspect of the present disclosure provides a method for preparing the crystal form A of entrectinib, wherein the method comprises the following steps:

adding a crude amorphous form of entrectinib into a mixed solvent of water and acetone, heating and refluxing for dissolution, gradually cooling to −5 to 20° C. for crystallization under an ultrasonic oscillation condition, filtering, and drying in air at room temperature to obtain the crystal form A of entrectinib.

A volume ratio of acetone to water is 1:0.1 to 1:2.0, preferably 1:0.8 to 1:1.5, and more preferably 1:1. A mass-to-volume ratio of the crude amorphous form of entrectinib to acetone is 1:5 to 1:40, preferably 1:7 to 1:20, and more preferably 1:8 to 1:15, in a unit of g/mL.

A third aspect of the present disclosure provides another method for preparing the crystal form A of entrectinib, wherein the method comprises the following steps:

adding a crude amorphous form of entrectinib into an organic solvent, heating for dissolution, adding water and a crystal seed of the crystal form A, cooling for crystallization, filtering, and drying to obtain the crystal form A of entrectinib.

The organic solvent is selected from one of isopropanol, acetone and acetonitrile or any mixed solvent thereof.

A volume ratio of the organic solvent to water is 1:0.1 to 1:2.0, preferably 1:0.8 to 1:1.5, and more preferably 1:1. A mass-to-volume ratio of the crude amorphous form of entrectinib to the organic solvent is 1:5 to 1:40, preferably 1:7 to 1:30, and more preferably 1:8 to 1:15, in a unit of g/mL.

An adding amount of the crystal seed is 0.1-1% of a feeding amount of the crude amorphous form of entrectinib.

The cooling for crystallization is performed at a temperature of −10 to 20° C., preferably-5 to 5° C.

A fourth aspect of the present disclosure provides another novel crystal form B of entrectinib, comprising diffraction peaks in an X-ray powder diffraction pattern using Cu-Kα radiation at 2θ angles of 8.5°±0.2°, 9.5°±0.2°, 10.4°±0.2°, 11.3°±0.2°, 14.4°±0.2°, 16.0°±0.2°, 18.5°±0.2°, 19.3°±0.2°, 20.5°±0.2°, and 22.3°±0.2°.

Preferably, the crystal form B of entrectinib comprises diffraction peaks in an X-ray powder diffraction pattern using Cu-Kα radiation at 2θ angles of 8.5°±0.2°, 9.5°±0.2°, 10.4°±0.2°, 11.3°±0.2°, 12.9°±0.2°, 13.8°±0.2°, 14.4°±0.2°, 16.0°±0.2°, 16.6°±0.2°, 17.4°±0.2°, 18.5°±0.2°, 19.3°±0.2°, 20.5°±0.2°, 22.3°±0.2°, 22.8°±0.2°, 23.9°±0.2°, 24.2°±0.2°, 25.5°±0.2°, and 30.1°±0.2°.

In a preferred embodiment of the present disclosure, the crystal form B of entrectinib has the following characteristic peaks and relative intensities under powder X-ray diffraction:

| 2θ | Relative intensity |
|---|---|
| 8.5° ± 0.2° | 91% |
| 9.5° ± 0.2° | 36% |
| 10.4° ± 0.2° | 75% |
| 11.3° ± 0.2° | 11% |
| 12.9° ± 0.2° | 9% |
| 13.8° ± 0.2° | 25% |
| 14.4° ± 0.2° | 74% |
| 16.0° ± 0.2° | 16% |
| 16.6° ± 0.2° | 16% |
| 17.4° ± 0.2° | 35% |
| 18.5° ± 0.2° | 56% |
| 19.3° ± 0.2° | 84% |
| 20.5° ± 0.2° | 93% |
| 22.3° ± 0.2° | 100% |
| 22.8° ± 0.2° | 88% |
| 23.9° ± 0.2° | 44% |
| 24.2° ± 0.2° | 32% |
| 25.5° ± 0.2° | 29% |
| 30.1° ± 0.2° | 16% |

In a preferred embodiment of the present disclosure, the crystal form B of entrectinib has an X-ray powder diffraction pattern substantially as shown in FIG. 3.

In one technical solution of the present disclosure, a DSC pattern of the crystal form B of entrectinib has a significant endothermic peak in the range of 182.3-207.4° C.; more specifically, a peak value of the endothermic peak appears at 196.5° C. In one technical solution of the present disclosure, the crystal form B of entrectinib has a DSC pattern substantially as shown in FIG. 4.

In one technical solution of the present disclosure, the crystal form B of entrectinib has a TGA pattern substantially as shown in FIG. 4.

A fifth aspect of the present disclosure provides a method for preparing the crystal form B of entrectinib, wherein the method comprises the following steps:

adding a crude amorphous form of entrectinib into dioxane, heating to 80° C. for dissolution, adding purified water, cooling to −5 to 20° C. for crystallization at a maintained temperature, filtering under sucking, and drying to obtain the crystal form B of entrectinib.

A volume ratio of dioxane to water is 1:0.2 to 1:2.0, preferably 1:0.6 to 1:1.4, and more preferably 1:0.8. A mass-to-volume ratio of the crude amorphous form of entrectinib to dioxane is 1:5 to 1:30, preferably 1:8 to 1:20, and more preferably 1:10 to 1:15, in a unit of g/mL.

Beneficial Effects

The crystal form A and the crystal form B of entrectinib provided by the present disclosure have higher purity, excellent chemical stability and crystal form stability, and better solubility, and are more suitable for industrial production. In addition, the existing experimental data demonstrates that the crystal form A and the crystal form B provided by the present disclosure show significant improvement and enhancement in one or more aspects of particle size, static electricity, fluidity and dissolution speed compared with existing crystal forms, overcome the defects in the prior art, are easy for drug preparation and industrial preparation, are simple to operate, and have good controllability.

DETAILED DESCRIPTION

Figure 1:
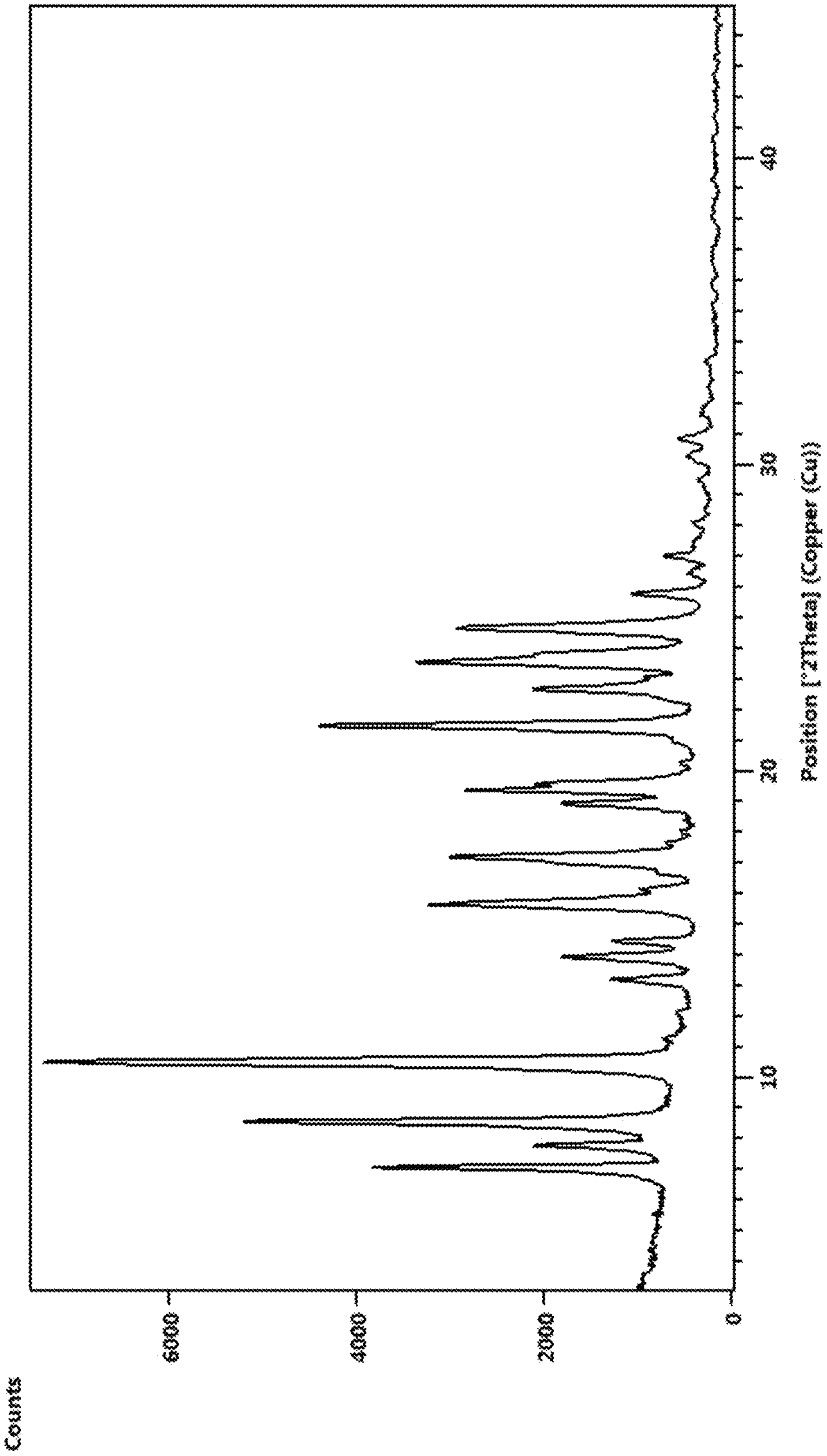
FIG. 1 is an X-RPD pattern of the crystal form A of entrectinib obtained in Example 2.

The above content of the present disclosure is further explained in detail by specific embodiments below, which yet shall not be construed as limiting the claimed subject matter of the present disclosure. All technical solutions implemented on the basis of the above content of the present disclosure fall within the scope of the present disclosure. The present disclosure describes generally and/or specifically with respect to the materials used in experiments and the experimental methods. Unless otherwise stated, the "room temperature" described in the present disclosure has the meaning generally known in the art, specifically refers to 15-35° C., preferably 20-30° C., and more preferably 20-25° C.

The instruments and methods used in the present disclosure:

(1) X-Ray Powder Diffractometer

Instrument Model: PANalytical X-Ray Powder Diffractometer

The experimental method was as follows: a ground sample (100 mg) was filled in a groove of a glass plate, the plane of the sample was made to the same level as the glass surface by using a glass slide, the sample was placed in a PANalytical X-ray powder diffractometer, and a 40 kV and 40 mA copper X-ray source was used, with a scanning range of 3-45° (2θ) and a scanning rate of 8°/min. The scanning error is typically ±0.2 degrees (2θ).

(2) TGA/DSC1 Simultaneous Thermal Analyzer

Instrument Model: METTLER TGA/DSC1.

The experimental method was as follows: a sample weighing 10 mg was placed in a closed aluminum pan with small pin holes, equilibrated at 30° C. and then heated to 250° C. at a scanning rate of 10° C./min. Dry nitrogen was used as the purge gas.

(3) Scanning Electron Microscope

Instrument Model: ZEISS Sigma 300 Scanning Electron Microscope

The experimental method was as follows: an appropriate amount of test sample was taken, uniformly spread on a conductive adhesive tape, sprayed with gold, and observed under an electron microscope.

Reference Example 1: Preparation of Crystal Form 1 of Entrectinib

Referring to the method in Example 1 of the document WO2013174876, that is, 5.5 g of a dried crude amorphous form of entrectinib was suspended in 130 mL of ethanol, heated and refluxed for 10 min; about 70 mL of ethanol was distilled before being cooled to room temperature. 110 mL of water was added, and a crystal seed was added to the suspension by using 55 mg of crystal form 1. The suspension was stirred for about 72 h and sampled to monitor the conversion to crystal form 1 by means of DSC. Finally, the suspension was filtered and dried to obtain 4.3 g of crystal form 1.

Reference Example 2: Preparation of Crystal Form 2 of Entrectinib

Referring to the method in Example 1 of the document WO2013174876, that is, 30 g of a dried crude amorphous form of entrectinib was suspended in 300 mL of ethanol, then 600 mL of purified water was added, and the suspension was filtered. Finally, the product was dried under vacuum to obtain about 26 g of crystal form 2 of entrectinib having an HPLC purity of 99.34%.

Reference Example 3: Preparation of Crystal Form 4 of Entrectinib

According to the method described in Example 1 of WO2017202674, 2 g of a dried crude amorphous form of entrectinib was suspended in 20 mL of ethanol (suspension A). 20 mL of suspension A was taken and heated to 60° C. to obtain a solution, and the solution was then cooled to room temperature. To the solution was added 20 mL of water to obtain a suspension and the precipitate was filtered. The product was dried under vacuum to obtain crystal form 4.

Reference Example 4: Referring to Example 1-1 of the Chinese Patent Application CN111171009A 2 g of the crystal form 2 of entrectinib and 10 mL of ethyl acetate were mixed, and the mixture was heated to 50° C. for dissolution, cooled to 10° C., and dried at room temperature to obtain a solid, namely the crystal form AZT-A named in the Chinese Patent Application CN111171009A.

Reference Example 5: Referring to Example 2-2 of the Chinese Patent Application CN111171009A 150 mg of the crystal form 2 of entrectinib was slurried in 6 mL of acetonitrile at 40° C. for 24 h, and the mixture was dried to obtain a solid, namely the crystal form AZT-B named in the Chinese Patent Application CN111171009A.

Reference Example 6: Referring to Example 5-2 of the Chinese Patent Application CN111171009A 0.3 g of the crystal form AZT-A of entrectinib obtained in Reference Example 4 was added into 1 mL of a mixed solvent of ethanol and purified water in a ratio of 3:1 at room temperature, and the mixture was stirred at 5° C. for 24 h to obtain a solid, namely the crystal form AZT-E named in the Chinese Patent Application CN111171009A.

Example 1: Preparation of Crystal Form A of Entrectinib 5.0 g of a crude amorphous form of entrectinib was added into 70 mL of acetone and 70 mL of purified water, and the mixture was heated and refluxed for dissolution. The mixture was gradually cooled to −5 to 20° C. for crystallization under an ultrasonic oscillation condition, filtered, and dried in air at room temperature to obtain 4.7 g of the crystal form A of entrectinib.

Figure 2:
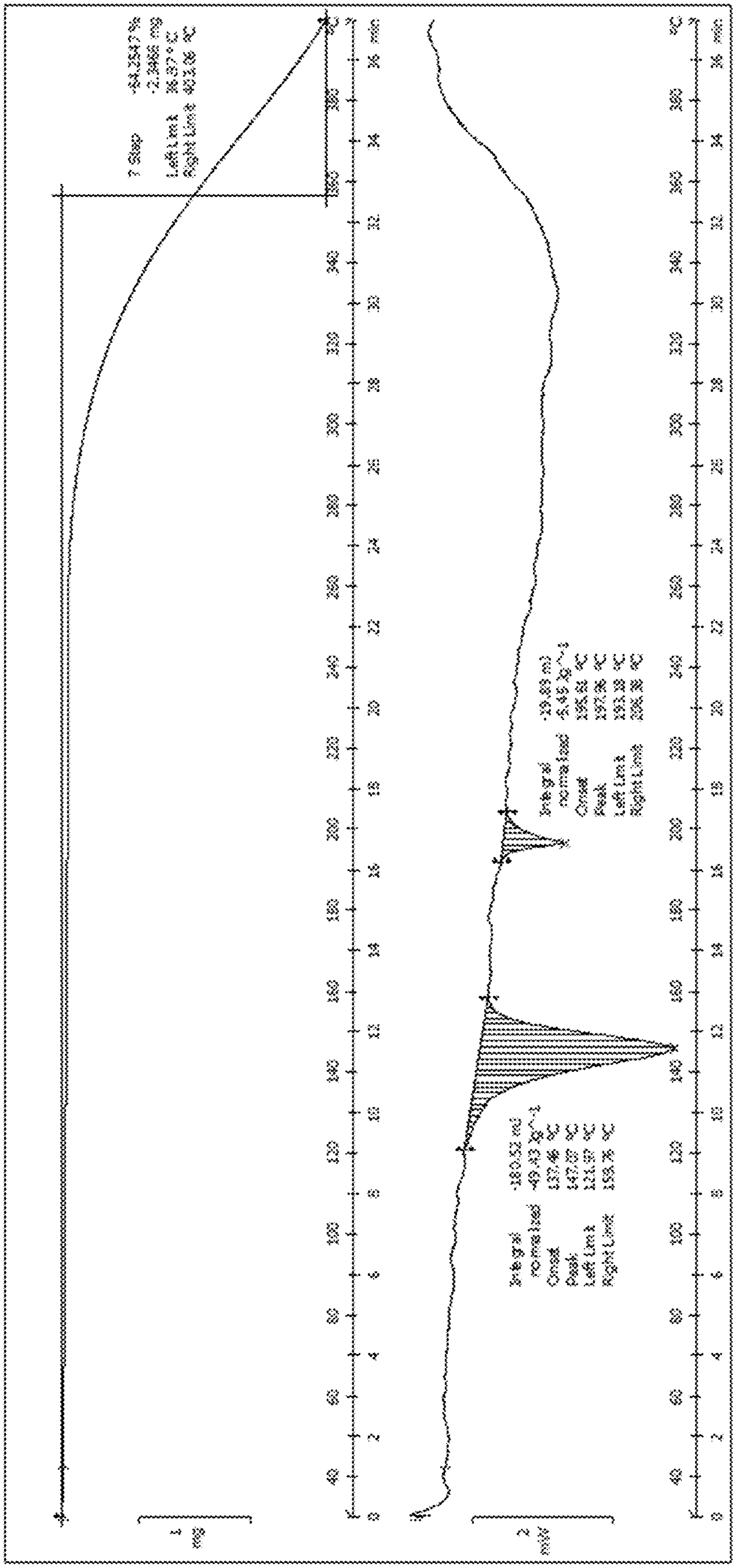
FIG. 2 is a DSC-TGA pattern of the crystal form A of entrectinib obtained in Example 2.

Through determination, the X-RPD pattern thereof is substantially consistent with FIG. 1, and the DSC-TGA pattern thereof is substantially consistent with FIG. 2.

Example 2: Preparation of Crystal Form A of Entrectinib 5 kg of a crude amorphous form of entrectinib was added into 50 L of acetone, and the mixture was heated and refluxed for dissolution. The mixture was cooled to 50-55° C., and then 20 L of purified water and 2 g of crystal seed of the crystal form A were added. The mixture was slowly cooled to −5 to 5° C. for crystallization at a maintained temperature, centrifuged, washed with purified water, and dried by blowing at 80±5° C. to obtain 4.5 kg of the crystal form A of entrectinib having an HPLC purity of 99.92%.

Through determination, the X-RPD pattern thereof is shown in FIG. 1, and the DSC-TGA pattern thereof is shown in FIG. 2.

Example 3: Preparation of Crystal Form A of Entrectinib 5.0 g of a crude amorphous form of entrectinib was added into 110 mL of isopropanol, and the mixture was heated and refluxed for dissolution. The mixture was cooled to 50-60° C., and then 11 mL of purified water and 5 mg of crystal seed of the crystal form A were added. The mixture was slowly cooled to −5 to 5° C. for crystallization at a maintained temperature, filtered under sucking, washed with purified water, and dried by blowing at 80±5° C. to obtain 4.4 kg of the crystal form A of entrectinib having an HPLC purity of 99.91%.

Through determination, the X-RPD pattern thereof is substantially consistent with FIG. 1, and the DSC-TGA pattern thereof is substantially consistent with FIG. 2.

Example 4: Preparation of Crystal Form A of Entrectinib 5.0 g of a crude amorphous form of entrectinib was added into 140 mL of acetonitrile, and the mixture was heated and refluxed for dissolution. The mixture was cooled to 50-60° C., and then 14 mL of purified water and 5 mg of crystal seed of the crystal form A were added. The mixture was slowly cooled to −5 to 5° C. for crystallization at a maintained temperature, filtered under sucking, washed with purified water, and dried by blowing at 80±5° C. to obtain 4.3 g of the crystal form A of entrectinib having an HPLC purity of 99.90%.

Through determination, the X-RPD pattern thereof is substantially consistent with FIG. 1, and the DSC-TGA pattern thereof is substantially consistent with FIG. 2.

Example 5: Preparation of Crystal Form B of Entrectinib 5.0 g of a crude amorphous form of entrectinib was added into 50 mL of dioxane, the mixture was heated to 80° C. for dissolution and cooled to 75° C., and then 40 mL of purified water was added. The mixture was slowly cooled to −5 to 5° C. for crystallization at a maintained temperature, filtered under sucking, washed with purified water, and dried by blowing at 80±5° C. to obtain 4.3 g of the crystal form B of entrectinib having an HPLC purity of 99.91%.

Figure 3:
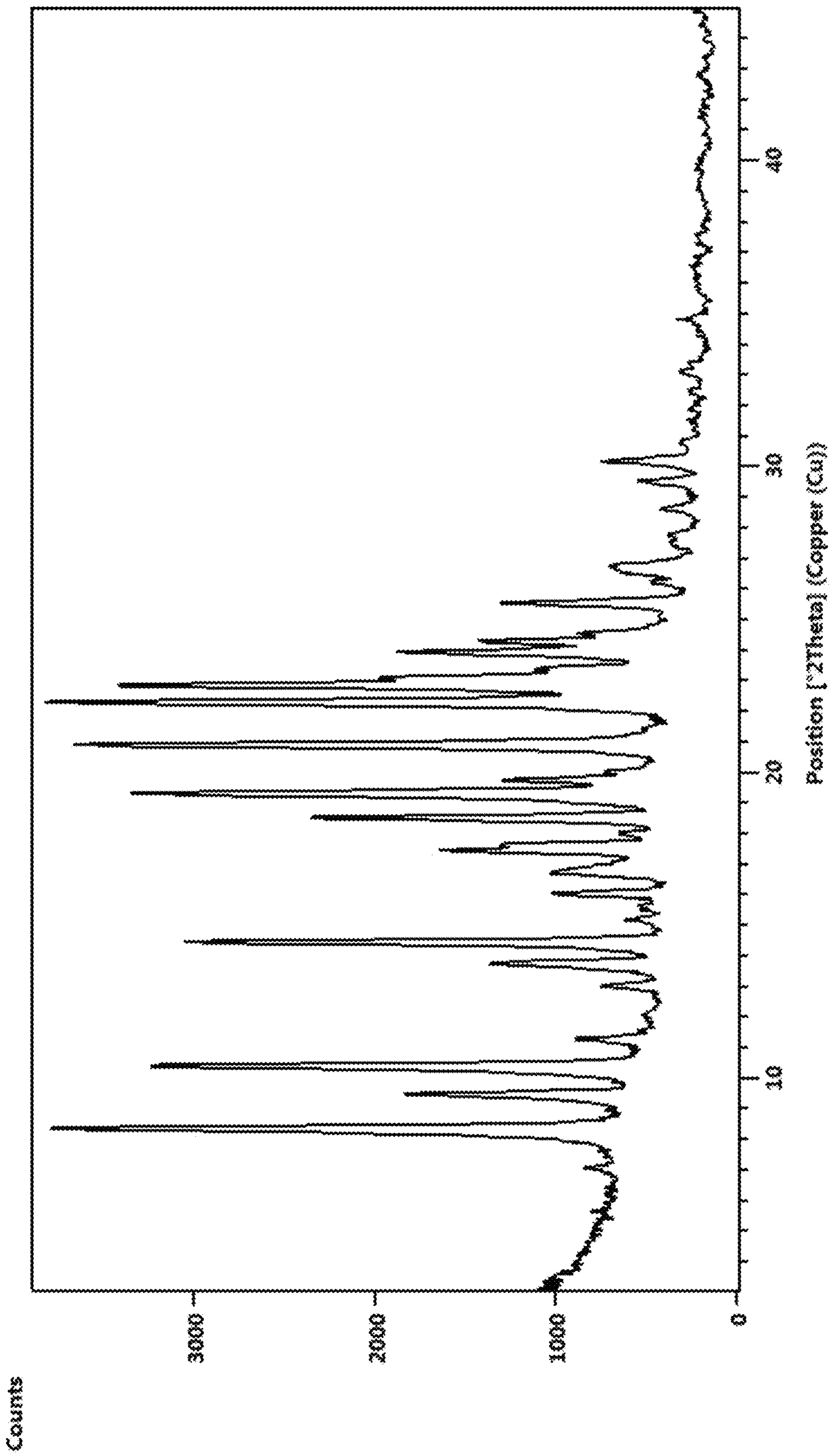
FIG. 3 is an X-RPD pattern of the crystal form B of entrectinib obtained in Example 5.
Figure 4:
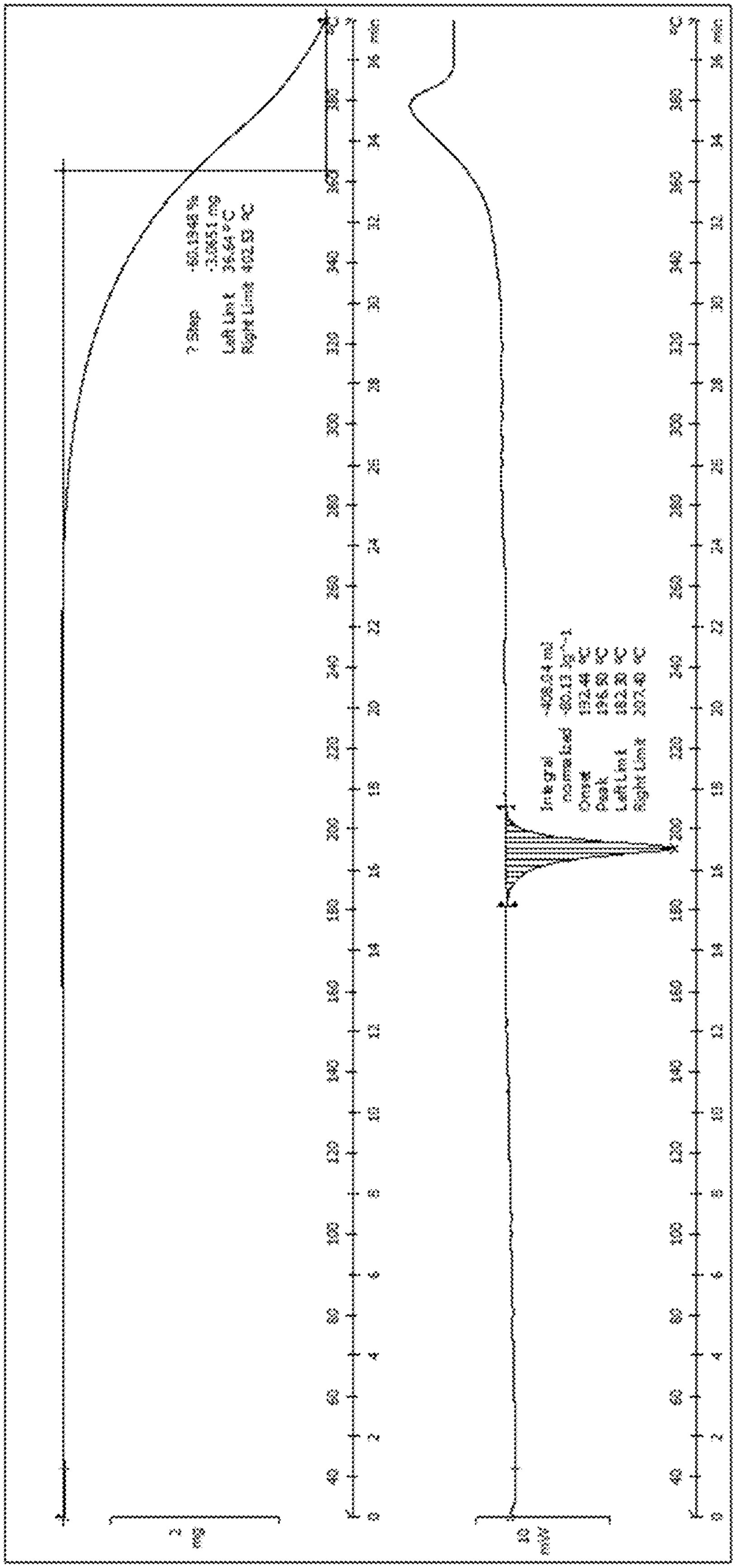
FIG. 4 is a DSC-TGA pattern of the crystal form B of entrectinib obtained in Example 5.
Figure 5:
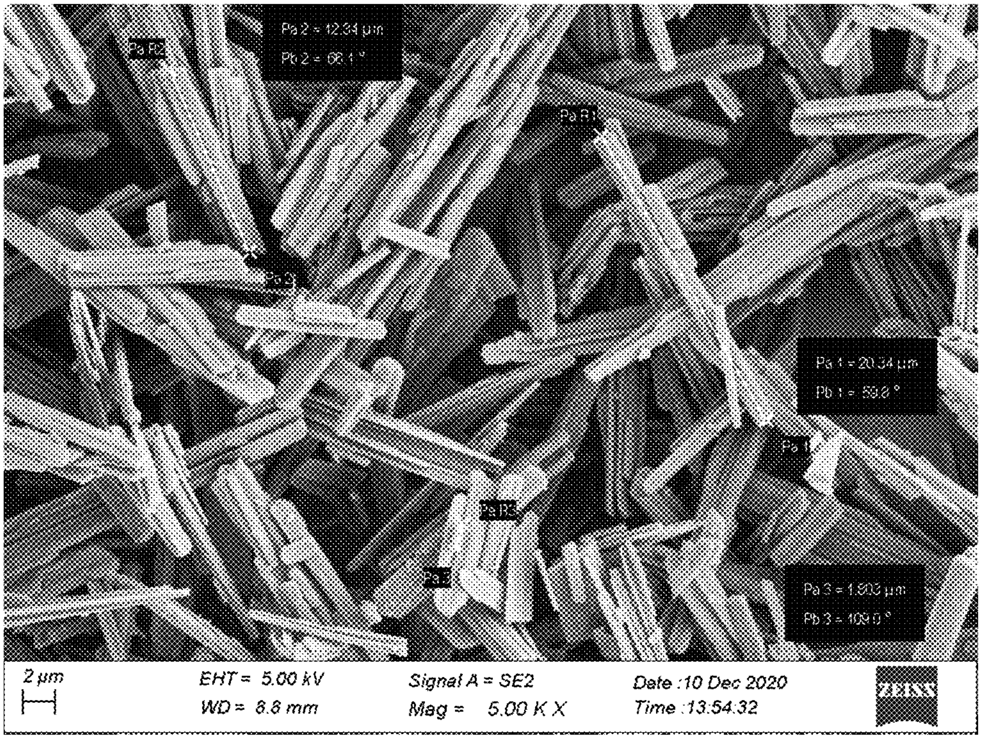
FIG. 5 is a scanning electron microscope image of the crystal form A of entrectinib obtained in Example 2.
Figure 6:
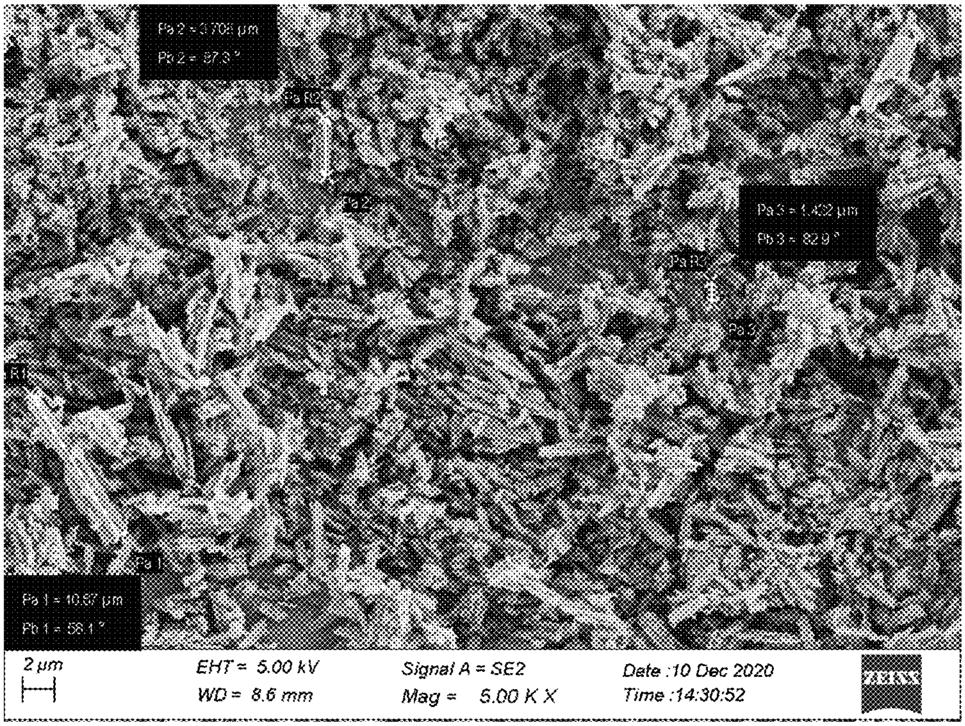
FIG. 6 is a scanning electron microscope image of the crystal form B of entrectinib obtained in Example 5.
Figure 7:
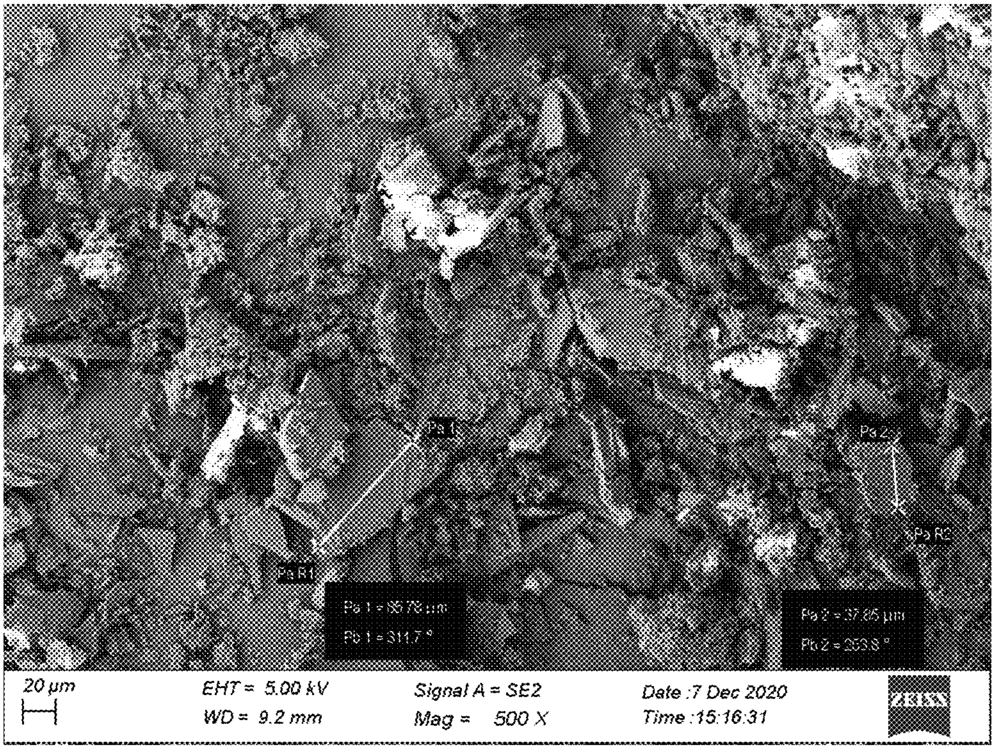
FIG. 7 is a scanning electron microscope image of the crystal form 2 obtained in Reference Example 2.
Figure 8:
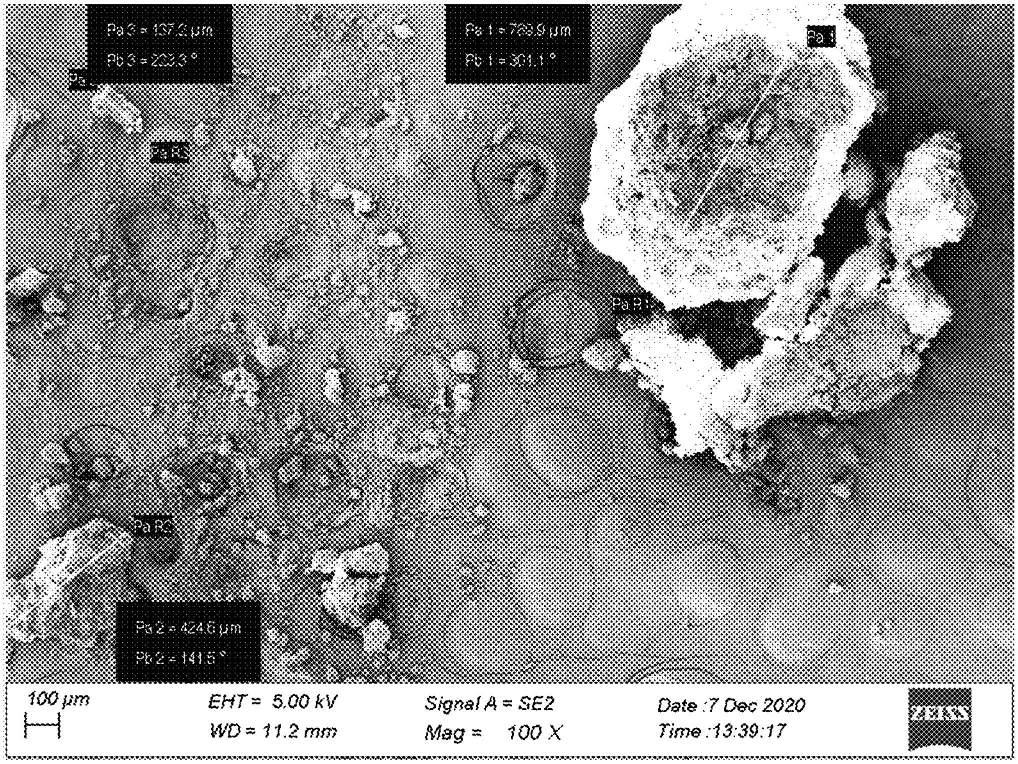
FIG. 8 is a scanning electron microscope image of the crystal form AZT-A obtained in Reference Example 4.
Figure 9:
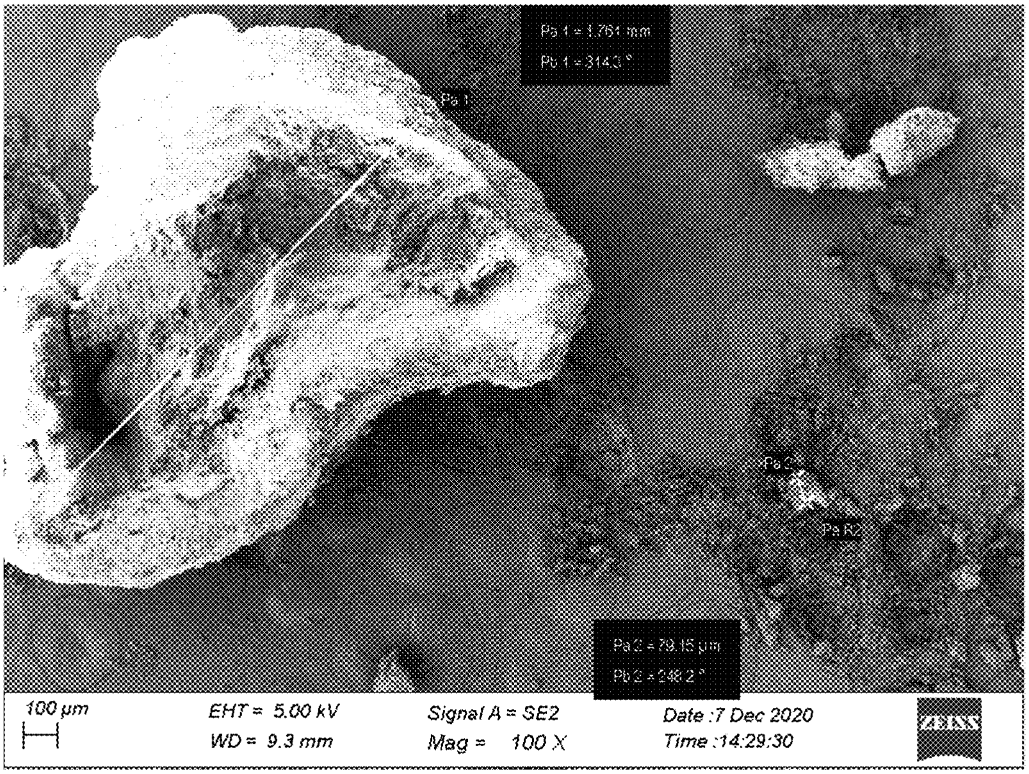
FIG. 9 is a scanning electron microscope image of the crystal form AZT-B obtained in Reference Example 5.
Figure 10:
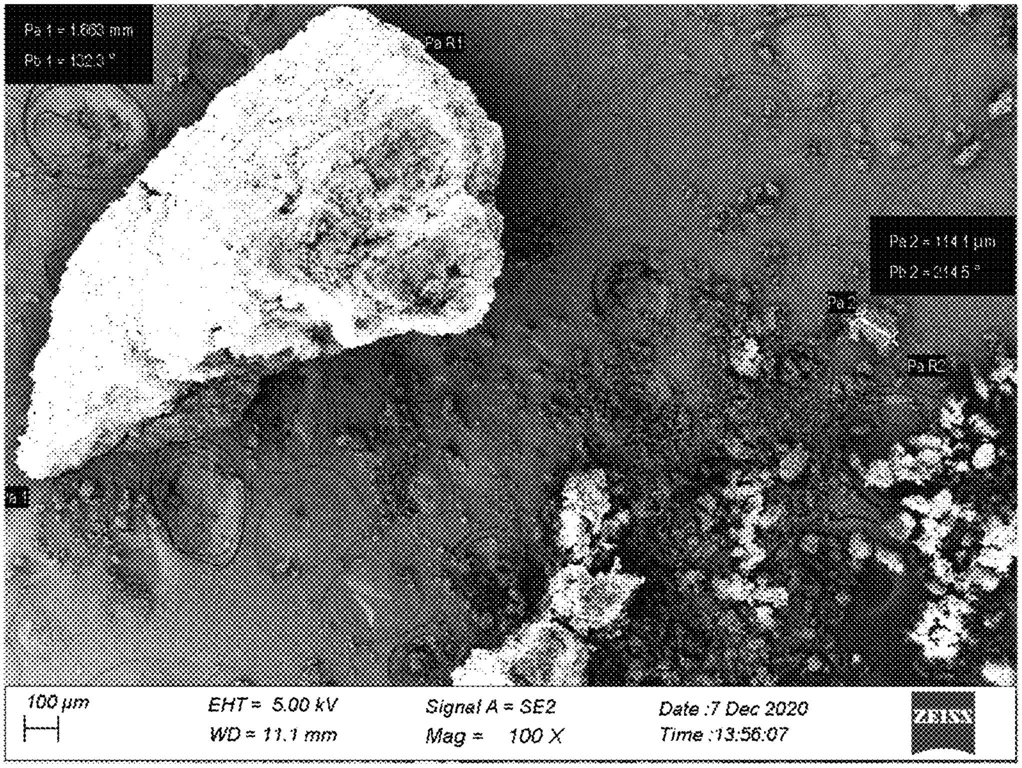
FIG. 10 is a scanning electron microscope image of the crystal form AZT-E obtained in Reference Example 6.

Through determination, the X-RPD pattern thereof is shown in FIG. 3, and the DSC-TGA pattern thereof is shown in FIG. 4.

Example 6: Preparation of Crystal Form B of Entrectinib 5.0 g of a crude amorphous form of entrectinib was added into 25 mL of dioxane, the mixture was heated to 80° C. for dissolution and cooled to 75° C., and then 15 mL of purified water was added. The mixture was slowly cooled to 0-10° C. for crystallization at a maintained temperature, filtered under sucking, washed with purified water, and dried in air at room temperature to obtain 4.2 g of the crystal form B of entrectinib having an HPLC purity of 99.90%.

Through determination, the X-RPD pattern thereof is substantially consistent with FIG. 3, and the DSC-TGA pattern thereof is substantially consistent with FIG. 4.

Example 7: Preparation of Crystal Form B of Entrectinib 5.0 g of a crude amorphous form of entrectinib was added into 100 mL of dioxane, the mixture was heated to 80° C. for dissolution and cooled to 75° C., and then 200 mL of purified water was added. The mixture was slowly cooled to 10-20° C. for crystallization at a maintained temperature, filtered under sucking, washed with purified water, and dried in air at room temperature to obtain 4.4 g of the crystal form B of entrectinib having an HPLC purity of 99.89%.

Through determination, the X-RPD pattern thereof is substantially consistent with FIG. 3, and the DSC-TGA pattern thereof is substantially consistent with FIG. 4.

Stability Test

Samples of the crystal form A of entrectinib prepared in Example 2, the crystal form A of entrectinib prepared in Example 5, the crystal form 1 (Reference Example 1), the crystal form 2 (Reference Example 2), and the crystal form 4 (Reference Example 3) were respectively placed under the condition of affecting factors, and the stability after the samples were placed for 10 days was tested. The test results are shown in Table 1.

For the specific method for testing the stability, reference could be made to high performance liquid chromatography in General Chapter 0512, *Chinese Pharmacopoeia*, Volume IV, 2015 Edition.

TABLE 1

Chemical stability test results

| Placement conditions | Placement time | Crystal form A of Example 2 Purity (%) | Crystal form B of Example 5 Purity (%) | Crystal form 1 of Reference Example 1 Purity (%) | Crystal form 2 of Reference Example 2 Purity (%) | Crystal form 4 of Reference Example 3 Purity (%) |
|---|---|---|---|---|---|---|
| / | 0 day | 99.92 | 99.91 | 99.21 | 99.34 | 99.29 |
| High temperature condition 60 °C | 10 days | 99.91 | 99.91 | 99.20 | 99.34 | 99.28 |
| High humidity condition 90% RH | 10 days | 99.92 | 99.90 | 99.20 | 99.33 | 99.29 |
| Light condition 5000 lux/h | 10 days | 99.91 | 99.91 | 99.19 | 99.33 | 99.28 |

TABLE 2

Crystal form stability test results

| Placement conditions | Placement time | Crystal form A of Example 2 | Crystal form B of Example 5 | Crystal form 1 of Reference Example 1 | Crystal form 2 of Reference Example 2 | Crystal form 4 of Reference Example 3 |
|---|---|---|---|---|---|---|
| / | 0 day | Crystal form A | Crystal form B | Crystal form 1 | Crystal form 2 | Crystal form 4 |
| High temperature condition 60 °C | 10 days | Crystal form A | Crystal form B | Crystal form 2 | Crystal form 2 | Crystal form 4 |
| High humidity condition 90% RH | 10 days | Crystal form A | Crystal form B | Crystal form 1 | Crystal form 2 | Crystal form 4 |
| Light condition 5000 lux/h | 10 days | Crystal form A | Crystal form B | Crystal form 1 | Crystal form 2 | Crystal form 4 |

As can be seen from Table 1, after a 10-day affecting factor test, the crystal form A and the crystal form B of the present disclosure have good chemical stability.

As can be seen from Table 2, after a 10-day affecting factor test, the crystal form A and the crystal form B of entrectinib prepared by the present disclosure have good crystal form stability, while the crystal form 1 in Reference Example 1 is unstable and shows crystal form conversion under a high temperature condition.

Solubility Comparison of Crystals

The solubility of the crystal form A, crystal form B, crystal form 2 (Reference Example 2), and crystal form 4 (Reference Example 3) of the present disclosure in 95% ethanol and an aqueous solution with pH=1 at 25° C. were respectively compared.

Test Conditions:

Dissolution temperature: 25° C.

Dissolution time: 20 min

The test results are as follows:

TABLE 3

Solubility comparison of crystal form A and crystal form B of entrectinib with crystal form 2 and crystal form 4 of the reference examples

| Sample | Solubility in 95% ethanol (mg/mL) | Solubility in aqueous solution with pH = 1 (mg/mL) |
|---|---|---|
| Crystal form A of Example 2 | 28.4 | 22.6 |
| Crystal form B of Example 5 | 26.2 | 21.0 |
| Crystal form 2 of Reference Example 2 | 21.1 | 19.1 |
| Crystal form 4 of Reference Example 3 | 20.5 | 18.8 |

The above data indicate that compared with the crystal form 2 and the crystal form 4 in the reference examples, the crystal forms A and B have better solubility in 95% ethanol and the aqueous solution with pH=1, and thus are more favorable for dissolution out of solid formulations.

Study on Preparation Stability of Crystal Forms

The crystal form A of entrectinib obtained in Example 2 was mixed and slurried respectively with the crystal form 2, the crystal form 4, and the crystal forms AZT-A, AZT-B and AZT-E obtained in the reference examples, and the conversion of the crystal forms was tested.

The mixing and slurring method was as follows: 0.1 g of each of the two crystal forms to be mixed was weighed and added into a single-necked flask. 2 mL of acetone and 1 mL of water were added. The mixture was stirred and slurried at room temperature for 10 h, filtered, and dried in air at room temperature to obtain crystals. The crystal forms were determined by X-RPD. The results are shown in the following table:

TABLE 4

Comparison of preparation stability of crystal forms

| Sample mixing | Converted crystal form |
|---|---|
| Crystal form A of Example 2 was mixed with crystal form 2 of Reference Example 2 | Crystal form A |
| Crystal form A of Example 2 was mixed with crystal form 4 of Reference Example 3 | Crystal form A |
| Crystal form A of Example 2 was mixed with crystal form AZT-A of Reference Example 4 | Crystal form A |
| Crystal form A of Example 2 was mixed with crystal form AZT-B of Reference Example 5 | Crystal form A |
| Crystal form A of Example 2 was mixed with crystal form AZT-E of Reference Example 6 | Crystal form A |

The experimental results show that when the crystal form A and other crystal forms were mixed together and slurried in an acetone/water system at room temperature for 10 h, the mixed crystal forms were all converted into the crystal form A, indicating that the crystal form A will not be subjected to crystal conversion under the system, while the other crystal forms will be subjected to crystal conversion. Therefore, the crystal form A is more stable and facilitated to preparation is.

Crystal Microscopic Morphology, Static Electricity, and Fluidity

The crystal form A obtained in Example 2, the crystal form B obtained in Example 5, the crystal form 2 of Reference Example 2, the crystal form AZT-A of Reference Example 4, the crystal form AZT-B of Reference Example 5, and the crystal form AZT-E of Reference Example 6 were taken, the microscopic morphologies were determined by a scanning electron microscope, and the crushing and fluidity were tested. The determination results are as follows.

TABLE 5

Comparison of crystal forms A and B of entrectinib with other crystal forms in terms of microscopic morphology, static electricity, and fluidity

| Sample | electron microscopy results of the crystal | Fluidity |
|---|---|---|
| Crystal form A of Example 2 | Rod-shaped, relatively uniform size, larger crystals with a length of about 20 μm | Loose powder, fine particles that require no crushing, having no static electricity and good fluidity |
| Crystal form B of Example 5 | Rod-shaped, relatively uniform size, larger crystals with a length of about 10 μm | Loose powder, fine particles that require no crushing, having no static electricity and good fluidity |
| Crystal form 2 of Reference Example 2 | Sheet-shaped, fragile, non-uniform size, larger crystals with a length of about 85 μm | Non-uniform crystal particle size, having large particles that require crushing, having relatively strong static electricity after crushing, and poor fluidity |
| Crystal form AZT-A of Reference Example 4 | Irregular bulk-shaped, non-uniform size, larger particles with a length of about 700 μm | Non-uniform crystal particle size, having large particles that require crushing, having strong static electricity after crushing, and poor fluidity |
| Crystal form AZT-B of Reference Example 5 | Irregular bulk-shaped, non-uniform size, larger particles with a length of more than about 1000 μm | Non-uniform crystal particle size, having large particles that require crushing, having strong static electricity after crushing, and poor fluidity |
| Crystal form AZT-E of Reference Example 6 | Irregular bulk-shaped, non-uniform size, larger particles with a length of more than about 1000 μm | Non-uniform crystal particle size, having large particles that require crushing, having strong static electricity after crushing, and poor fluidity |

The above results show that the crystal forms A and B of the present disclosure have fine particles, do not need to be crushed, and have good fluidity; while the crystal form 2 has a non-uniform crystal particle size and has large particles, relatively strong static electricity after being crushed, and poor fluidity; the crystal forms AZT-A, AZT-B and AZT-E have overlarge particles, relatively strong static electricity after being crushed, and poor fluidity. Because the crystal forms in the reference examples have relatively strong static electricity and poor fluidity, these characteristics not only affect the uniformity of mixed powder of the API, but also have extremely adverse effects on the preparation of solid formulations.

The embodiments of the present disclosure have been described above. However, the present disclosure is not limited to the embodiments described above. Any modification, equivalent, improvement and the like made without departing from the spirit and principle of the present disclosure shall fall within the protection scope of the present disclosure.

The invention claimed is:

1. A crystal form A of entrectinib of formula I:

(I)

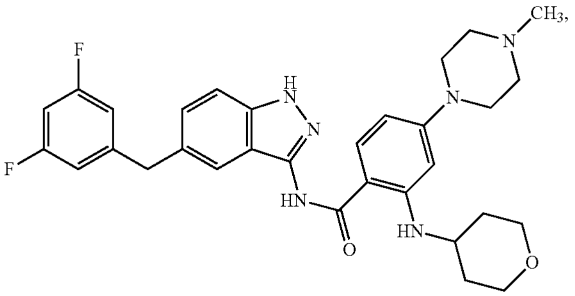

comprising characteristic diffraction peaks in an X-ray powder diffraction pattern using Cu-Kα radiation at 2θ angles of 7.1°±0.2°, 7.7°±0.2°, 8.5°±0.2°, 10.5°±0.2°, 13.9°±0.2°, 15.6°±0.2°, and 21.5°±0.2°.

2. A method for preparing the crystal form A of entrectinib according to claim 1, comprising:

adding a crude amorphous form of entrectinib into a mixed solvent of water and acetone, heating and refluxing for dissolution, cooling to −5 to 20° C. for crystallization under an ultrasonic oscillation condition, filtering, and drying in air at room temperature to obtain the crystal form A of entrectinib.

3. The method according to claim 2, wherein a volume ratio of acetone to water is 1:0.1 to 1:2.0; and a mass-to-volume ratio of the crude amorphous form of entrectinib to acetone is 1:5 to 1:40, in a unit of g/mL.

4. A method for preparing the crystal form A of entrectinib according to claim 1, comprising:

adding a crude amorphous form of entrectinib into an organic solvent, heating for dissolution, adding water and a crystal seed of the crystal form A, cooling for crystallization, filtering, and drying to obtain the crystal form A of entrectinib, wherein the organic solvent is selected from isopropanol, acetone, acetonitrile, and mixtures thereof.

5. The method according to claim 4, wherein a volume ratio of the organic solvent to water is 1:0.1 to 1:2.0; a mass-to-volume ratio of the crude amorphous form of entrectinib to the organic solvent is 1:5 to 1:40, in a unit of g/mL; an added amount of the crystal seed is 0.1-1% of a feeding amount of the crude amorphous form of entrectinib; and the cooling for crystallization is performed at a temperature of −10 to 20° C.

6. The method according to claim 2, wherein a volume ratio of acetone to water is 1:0.8 to 1:1.5; and a mass-to-volume ratio of the crude amorphous form of entrectinib to acetone is 1:7 to 1:20, in a unit of g/mL.

7. The method according to claim 4, wherein a volume ratio of the organic solvent to water is 1:0.8 to 1:1.5; and a mass-to-volume ratio of the crude amorphous form of entrectinib to the organic solvent is 1:7 to 1:30, in a unit of g/mL.

* * * * *